(12) United States Patent
Staats

(10) Patent No.: US 6,925,390 B2
(45) Date of Patent: Aug. 2, 2005

(54) CUSTOMIZED MICROFLUIDIC DEVICE DESIGN, ORDERING, AND MANUFACTURING

(76) Inventor: Sau Lan Tang Staats, 609 Ramsey Rd., Hockessin, DE (US) 19707

( * ) Notice: Subject to any disclaimer, the term of this patent is extended or adjusted under 35 U.S.C. 154(b) by 0 days.

(21) Appl. No.: 10/164,022

(22) Filed: Jun. 6, 2002

(65) Prior Publication Data

US 2004/0260418 A1 Dec. 23, 2004

Related U.S. Application Data

(63) Continuation-in-part of application No. PCT/US02/02704, filed on Jan. 30, 2002, and a continuation-in-part of application No. 10/046,362, filed on Jan. 14, 2002.

(60) Provisional application No. 60/265,431, filed on Jan. 31, 2001, provisional application No. 60/261,581, filed on Jan. 15, 2001, provisional application No. 60/261,584, filed on Jan. 15, 2001, provisional application No. 60/310,337, filed on Aug. 6, 2001, provisional application No. 60/341,069, filed on Dec. 19, 2001, provisional application No. 60/338,696, filed on Dec. 11, 2001, and provisional application No. 60/378,881, filed on May 8, 2002.

(51) Int. Cl.$^7$ ............................................. G06F 11/00
(52) U.S. Cl. ............................................. 702/19; 700/97
(58) Field of Search .............................. 702/19; 700/97, 700/182; 703/1, 9; 345/964

(56) References Cited

U.S. PATENT DOCUMENTS

| | | | |
|---|---|---|---|
| 4,756,884 A | 7/1988 | Hillman et al. | |
| 5,486,335 A | 1/1996 | Wilding et al. | |
| 5,900,130 A | 5/1999 | Benvegnu et al. | |
| 5,992,820 A | 11/1999 | Fare et al. | |
| 6,647,305 B1 | * 11/2003 | Bigelow | 700/97 |
| 2002/0183996 A1 | * 12/2002 | Lee et al. | 703/9 |

* cited by examiner

Primary Examiner—Marc S. Hoff
Assistant Examiner—Edward Raymond
(74) Attorney, Agent, or Firm—Darby & Darby

(57) ABSTRACT

Processes and systems are described for designing microfluidic devices, via an interactive process involving communication between a requestor and a provider over an electronic network.

20 Claims, 9 Drawing Sheets

X – X'

X-X'

CUSTOMIZED MICROFLUIDIC DEVICE DESIGN, ORDERING, AND MANUFACTURING

CROSS-REFERENCE TO RELATED APPLICATIONS

This application is a continuation-in-part of PCT/US 02/02704, filed on Jan. 30, 2002, which claims priority to U.S. Provisional Application Ser. No. 60/265,431 filed Jan. 31, 2001, and is also a continuation-in part of U.S. application Ser. No. 10/046,362, filed Jan. 14, 2002, which claims priority to U.S. Provisional Application Ser. No. 60/261,581 and 60/261,584, both filed on Jan. 15, 2001. This application also claims priority to U.S. Provisional Application Ser. No. 60/310,337 filed Aug. 6, 2001; U.S. Provisional Application Ser. No. 60/341,069 filed Dec. 19, 2001; U.S. Provisional Application Ser. No. 60/338,696 filed Dec. 11, 2001, titled FLUIDIC DEVICES AND METHODS FOR TWO-DIMENSIONAL SEPARATIONS, and a U.S. Provisional Application Ser. No. 60/378,881 titled MICROFLUIDIC DEVICES WITH VARIABLE CONFIGURATIONS ON POLYMER SUBSTRATES filed May 8, 2002. All of the above applications have been filed in the name of the common inventor of the present application, Sau Lan Tang Staats, and are incorporated herein by reference.

FIELD OF THE INVENTION

This invention relates to microfluidic devices. More particularly, it relates to a method of providing a customized microfluidic device via an interactive design process involving a requester and a provider.

BACKGROUND OF THE INVENTION

A microfluidic, or lab-on-a-chip (LOC), device is a planar device, one surface of which contains one or more of the following microfluidic features: intersecting channels, reservoirs, valves, detectors, flow switches, etc., which are fabricated using semiconductor microfabrication technology. The device surface is typically bonded to another planar surface so that the channels are enclosed except at sample and buffer input and output points. Microfluidic devices are designed for complex laboratory functions such as DNA sequencing, analytical separation and analytical measurements. The first of such devices disclosed in the patent literature were made of silicon, as described by Pace, U.S. Pat. No. 4,908,112.

Microfluidic devices are considered the enabling technology for low cost, high versatility operations, many of which find great utility in biotech and pharmaceutical industries. Applications of planar microfabricated devices primarily include using electroosmotic, electrokinetic, and/or pressure-driven motions of liquids and particles for fluid transport. The proceedings of the Micro Total Analysis Systems-2000 Symposium (A. Van Den Berg and W. Olthuis, ed., Kluwer Academic Publishers, Dordrecht (2000)) highlight the recent rapid progress in the field of microfluidics.

A common means of injecting samples into the enclosed fluid channels for analytical operations such as capillary electrophoresis (CE) is the use of intersecting channels to connect the sample reservoirs to the main fluid separation channels. The intersecting channels can be in the form of a 'T', as first disclosed in U.S. Pat. No. 4,908,112, or in the form of a cross, as shown in FIG. 1. Referring to FIG. 1, a sample to be injected from the sample reservoir 1 to the fluidic channel by an electrokinetically driven operation requires a voltage Vs to be applied to the sample reservoir or well. Another voltage or electrical ground Vsw is applied to the sample waste well 2, typically situated beyond the junction point of the sample injection channel and the main fluidic channel. A stream of the sample is electrokinetically transported from the sample reservoir toward the waste reservoir, intersecting the main fluidic channel connecting buffer reservoir 3 and buffer waste well 4 en route. An injection plug of sample into the main fluidic channel is formed when the voltage difference Vs-Vsw is reduced or eliminated, thus stopping the stream, and another voltage, Vb, is applied to the buffer reservoir 3 and, a voltage Vbw to the buffer waste well 4. In this mode of sample injection, a sample reservoir, a buffer reservoir and at least one waste well are typically provided. Even when only several nanoliters of sample is desired for the separation experiment, a much larger quantity of sample is typically placed in the sample reservoir to establish the flow toward the main microfluidic channel, which may be the CE separation channel.

If automatic sample filling of the device is desired, as in the case of 96-channel CE devices for high-throughput applications, a coupler such as that described in E. Meng et al., Proceedings for Micro-TAS 2000, ibid. Pp. 41–44 can be used to couple the sample from an external vessel into the sample reservoir on the device via a capillary. Once the sample is deposited into the sample reservoir, the same injection procedure as described above may be carried out.

In liquid phase applications, especially in capillary electrophoresis, the channel widths used by those skilled in the art are generally uniform in width, with the most common width being about 100 $\mu$m or smaller.

It is believed that LOC may be used to perform a variety of operations that are currently performed by other laboratory methods. Unfortunately, only few people are currently skilled in the art of making and using LOC devices. Many of the most attractive customers for LOC technology are scientists who are experts in their specific fields of science and are well-versed in performing experiments using traditional lab techniques, but who are not yet familiar with LOC. Accordingly, such scientists may need substantial guidance in converting their traditional lab techniques to LOC technology. For someone skilled in LOC technology, designing an LOC device is relatively straightforward, once certain parameters of the laboratory technique to be replicated are known. Thus, typically, an LOC technologist discusses with the laboratory scientist the parameters of the operation to be replicated via LOC, and then designs the LOC device. This approach, while effective in producing a functionally suitable device, suffers from the delay and expense inherent in arranging meetings among the parties involved. Furthermore, the cost of prototyping an LOC device with conventional microfabrication technology involving cleanroom techniques or laser cutting is expensive.

As can be appreciated from the above, there is a need for a more facile means by which the laboratory scientist can quickly identify a configuration for a microfluidic device which will perform functions that he can identify, but for which he has no design expertise, and then rapidly obtain the designed device.

SUMMARY OF THE INVENTION

In one aspect the invention comprises a method for designing a microfluidic device, the method comprising the steps of providing an interactive interface, accessible over a computer information network, for designing one or more microfluidic devices; receiving from a requestor at the interactive interface via the computer information network a request to design a microfluidic device; prompting the requestor for information about desired operational steps to be performed by the microfluidic device; receiving and storing the information about the desired operational steps from the requestor; providing a CAD interface having access to a database of microfluidic device component designs corresponding to a plurality of operational steps performable by microfluidic devices; and using the CAD interface to generate a visual display of the microfluidic device viewable by the requestor via the computer information network, the visual display compiled using microfluidic device component designs corresponding to the desired operational steps for the microfluidic device.

In another aspect, the invention comprises a system for designing a microfluidic device, the system comprising an interactive computer interface accessible by a computer information network for designing one or more microfluidic devices, the interactive computer interface adapted to receive from a requestor a request to design a microfluidic device, prompt the requestor for information about desired operational steps to be performed by the microfluidic device, and receive information about the desired operational steps from the requester; a first computer memory for storing the information received from the requester about the desired operational steps; a computerized database of microfluidic device component designs corresponding to a plurality of operational steps performable by microfluidic devices; and a CAD interface in communication with the interactive computer interface, the first computer memory, and the computerized database for compiling a plurality of microfluidic device component designs corresponding to the desired operational steps for the microfluidic device into a visual display of the microfluidic device viewable by the requester via the computer information network.

In a further aspect, the invention comprises a method for providing a microfluidic device, the method comprising the steps of providing an interactive interface, accessible over a computer information network, for designing one or more microfluidic devices; receiving from a requestor at the interactive interface via the computer information network a request to design a microfluidic device; prompting the requestor for information about desired operational steps to be performed by the microfluidic device; receiving and storing the information about the desired operational steps from the requestor; providing a CAD interface having access to a database of microfluidic device component designs corresponding to a plurality of operational steps performable by microfluidic devices; using the CAD interface to generate a visual display of the microfluidic device viewable by the requester via the computer information network, the visual display compiled using microfluidic device component designs corresponding to the desired operational steps for the microfluidic device; receiving at the interactive interface via the computer information network, a purchase order for the microfluidic device; sending information defining said microfluidic device to a manufacturing facility; and manufacturing said microfluidic device. The method further comprises performing all of these steps with respect to a first iteration of a microfluidic device, and further comprises repeating all but the first step with respect to a second iteration of the microfluidic device, wherein the information about the desired operational steps with respect to the first iteration is made available to the requestor for modification in designing the second iteration, wherein the information about the operational steps comprises functional information, scale information, sequence information, or a combination thereof, the computer information network comprises a global computer information network, and the manufacturing facility comprises a CAM interface in communication with the CAD interface.

It is to be understood that both the foregoing general description and the following detailed description are exemplary, but are not restrictive, of the invention.

BRIEF DESCRIPTION OF DRAWINGS

The invention is best understood from the following detailed description when read in connection with the accompanying drawings, which illustrate the diversity of designs, and potential complexity, available according to this invention. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

In order to describe the invention in all of its detail, it is useful to first discuss the types and variety of possible device designs. Then, based on an understanding of the design objectives, an explanation of the methods and means of designing, ordering, and manufacturing can be addressed.

Exemplary Microfluidic Device Designs

In all of its aspects, the invention involves designing configurations for microfluidic devices. Following are examples of the types of devices that can be designed by the methods of this invention. The listing is not exhaustive, but serves to illustrate the variety and complexity of designs possible for microfluidic devices, and the desirability of affording facile ways of designing and delivering them.

Figure 1:
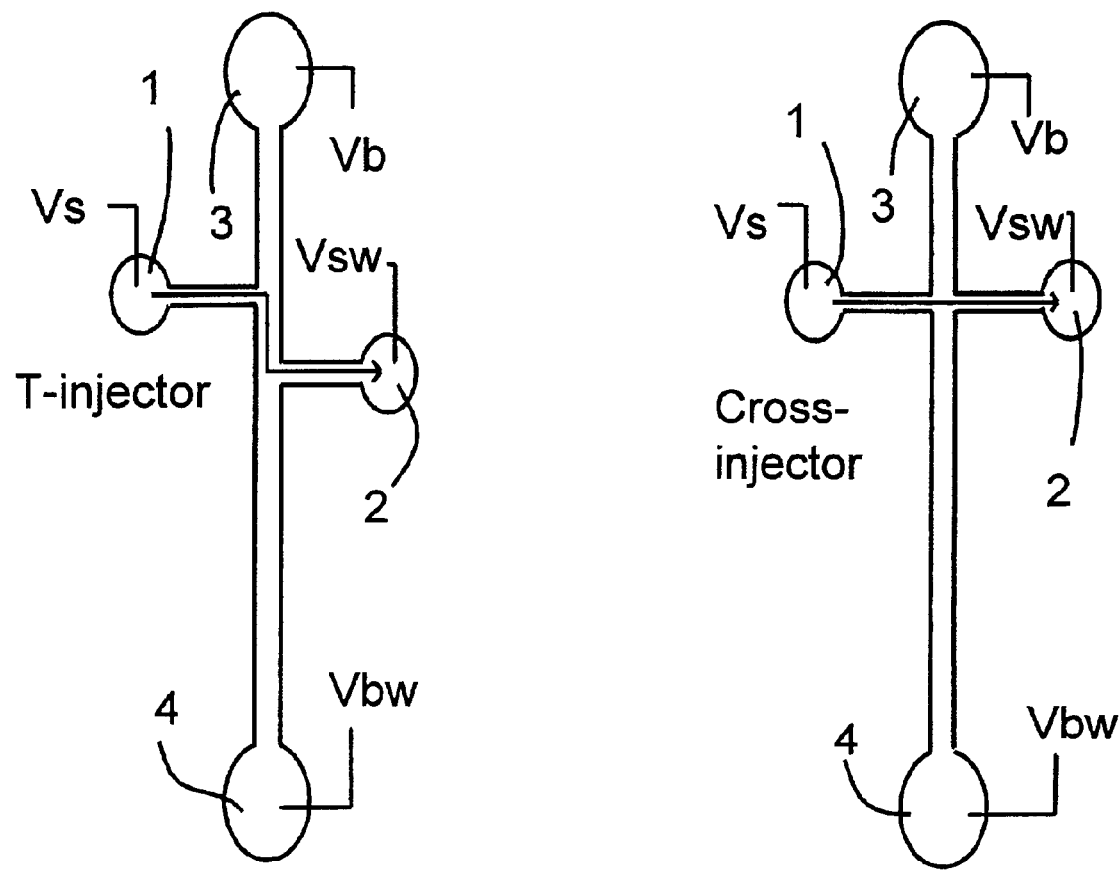
FIG. 1 is a schematic drawing showing the 'T' or 'cross' configurations for sample injection commonly used in LOC devices in common use.
Figure 2:
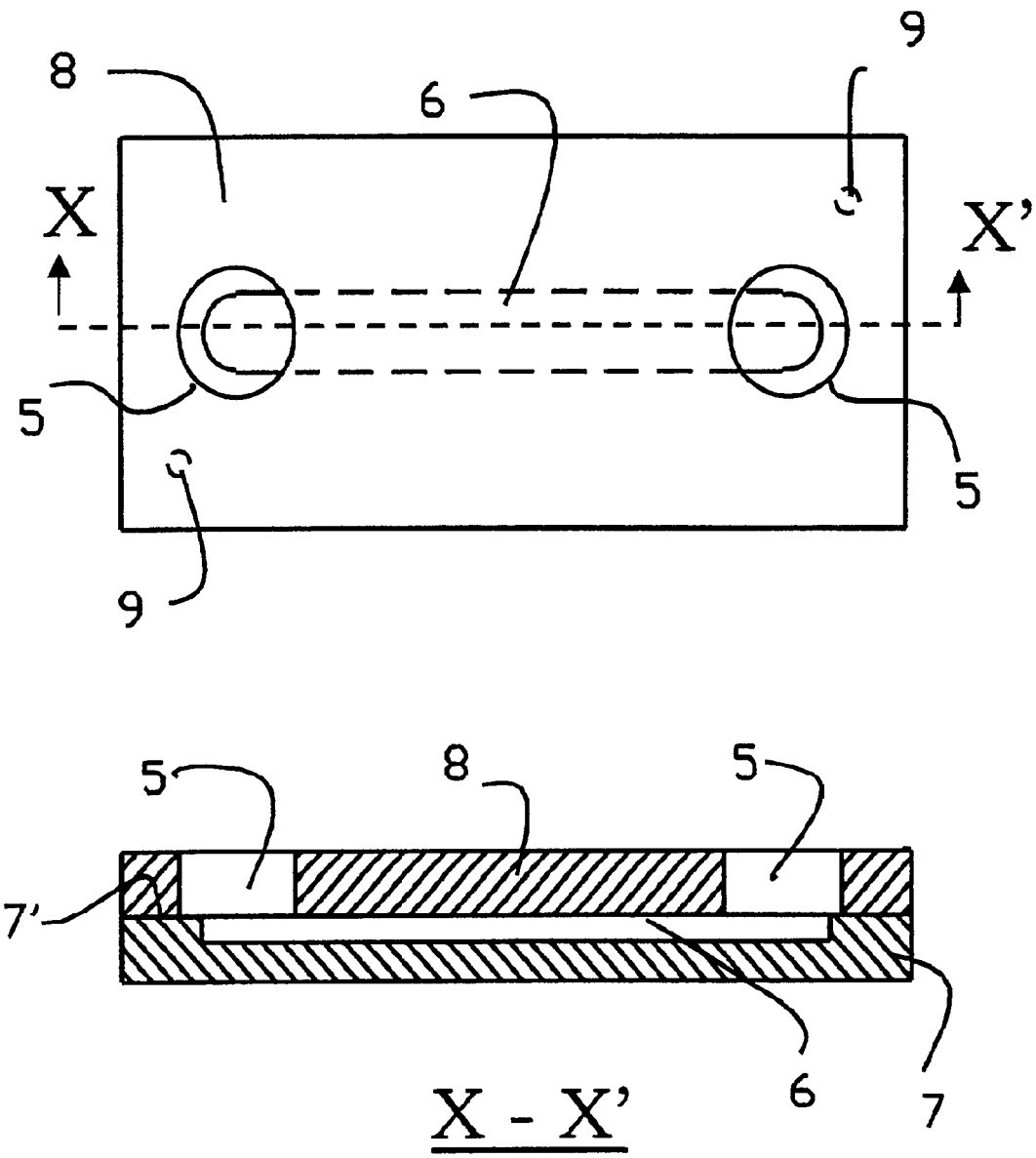
FIG. 2 shows top and section schematic views of a simple microfluidic lab-on-a-chip device with a buried channel.

The microfluidic devices designable by the methods of the present invention can for example allow sample injection and separation to be carried out in a single channel. Referring now to the drawings, wherein like reference numerals refer to like elements throughout, FIG. 2 shows top and section views of a schematic representation of a microfluidic device such as can be designed according to the present invention, with a substrate 7 and a single channel 6 therein. The substrate has a top surface 7' and a cover piece 8 is shown positioned above the substrate 7.

Channel 6 has a bottom and a sidewall, and a defined width. The microfluidic channel 6 has a width larger than 100 μm, preferably larger than 150 μm. The depth of the channel is defined by the height of the sidewall and is preferably between 10 and 100 μm. The larger dimensions of the channel structures shown in FIG. 2 are conducive to the relative ease of fabricating microfluidic features such as microfluidic channels and access ports in a single step in polymeric substrate materials. The device shown in FIG. 2 comprises a channel wherein the bottom of the channel is co-planar with a plane beneath the top surface of the substrate. The channel shown in FIG. 2 is herein referred to as a buried channel. As described in more detail below, the channel bottom may be coplanar with the top surface of the substrate, as shown in FIG. 3B, and this channel architecture is herein referred to as a raised channel.

As shown in FIG. 2, the cover 8 has access ports 5 that align with channel 6. The access ports 5 are aligned with the microfluidic channel by means of locating devices 9 shown in this diagram as dowel pins, but may be other kinds of location devices capable of aligning two separate pieces to an accuracy of 0.001 inch (25 μm) or better.

To aid the alignment of the access port in the cover to the channel, or in the alignment of one channel to a channel in another substrate, locating devices such as dowel pins, locating edges, protrusions from the substrate or cover or other locating devices that accurately align separate pieces may be incorporated into the substrates. The relatively large width of the channel in this design allows alignment to within 25 μm or 0.001 inch. Such accuracy is feasible with current alignment devices.

Figure 4:
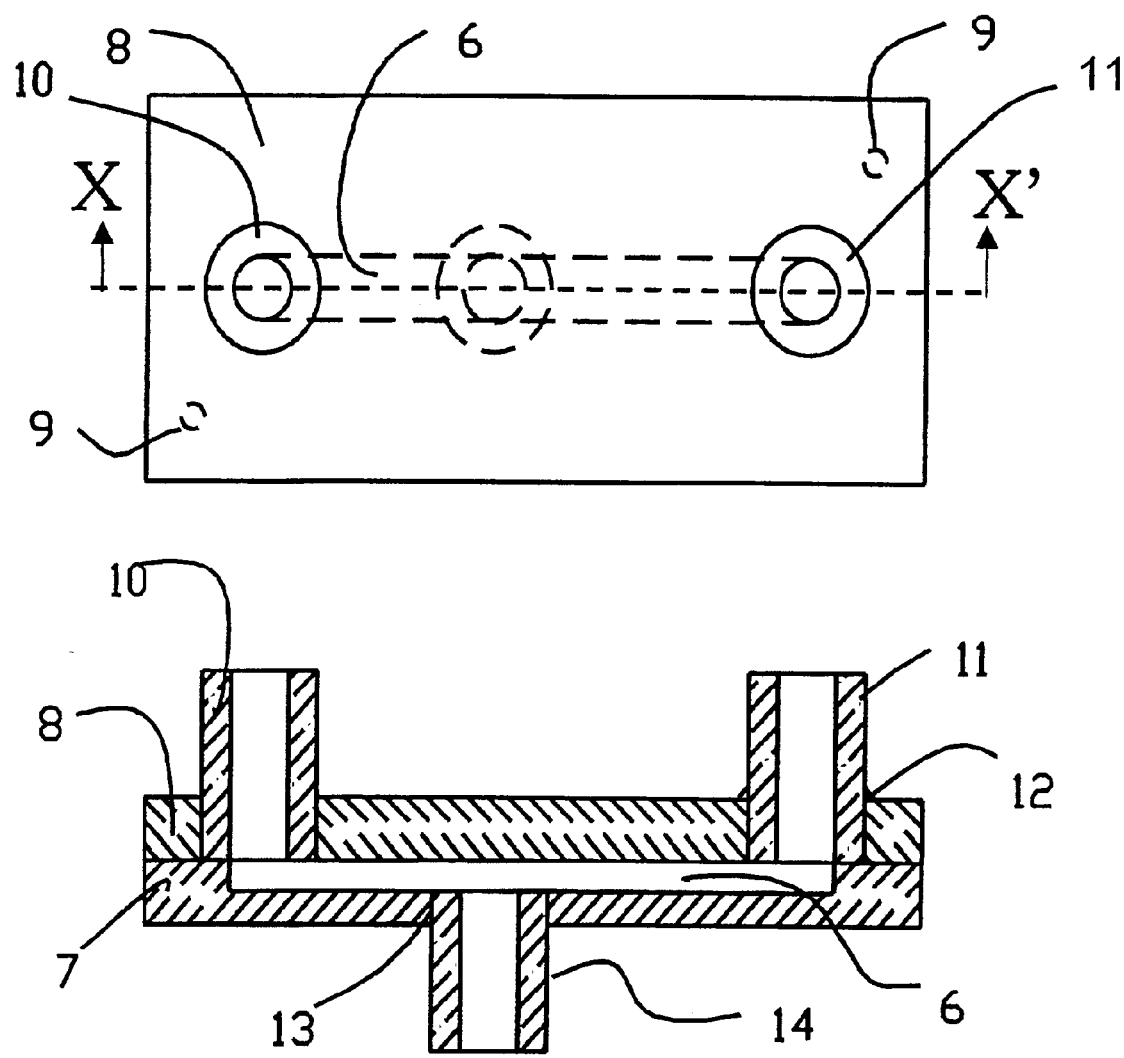
FIG. 4 shows a schematic of a microfluidic lab-on-a-chip device with a capillary connected to the microfluidic channel.

The access ports may be in the cover that is joined mechanically or bonded to the surface of the substrate containing the microfluidic channel to seal the channel, as shown in FIG. 2, or alternatively the access port may also be at the bottom of the channel such that the opening of the hole goes through at least part of the thickness of the substrate, as shown in FIG. 4. At places along the channel where sample injection is desired, an access port will be positioned. The access ports are preferably round and have an internal cross-sectional area approximately the same as the cross-sectional area of the channel. The access port and the channel may be aligned to minimize turbulent flow of the fluid due to a mismatch of the internal volumes when the fluid flows from the capillary into the microfluidic channel.

The access ports, whether formed in the cover or below the channel, or in another substrate aligned with the channel substrate, provide access to the channel from either above or below the plane of the channel. This architecture obviates the need for intersecting channels on the same plane for sample injection purposes. Because the channel architecture eliminates the need for samples to be stored for loading purposes on the device, sample and buffer amounts are limited to only the amount consumed by the device operation. This is advantageous in situations when very minute amounts of the sample are available. With such channel architecture, a substrate with a top surface comprising a plurality of non-intersecting channels can be used to perform microfluidic functions by providing interconnections between channels and other devices through connections existing outside the plane of the substrate surface.

The cover and substrate of the microfabricated microfluidic devices designable by the methods and systems of this invention may both be formed of the same types of materials, such as glass, quartz, various polymers, insulating materials such as ceramics, and semi-conducting materials such as silicon. Alternatively, the cover may be made of one material and the substrate may be made of a different material. In particular, the cover may be made of quartz and the substrate with the microfabricated features may be made of an elastomer such as polydimethylsiloxane (PDMS). Stacked structures comprising multiple layers of substrates may be made of the same material or different materials. The microfluidic features within such a stacked device may be aligned accurately from layer to layer using mechanical alignment means as described herein.

Figure 3A:
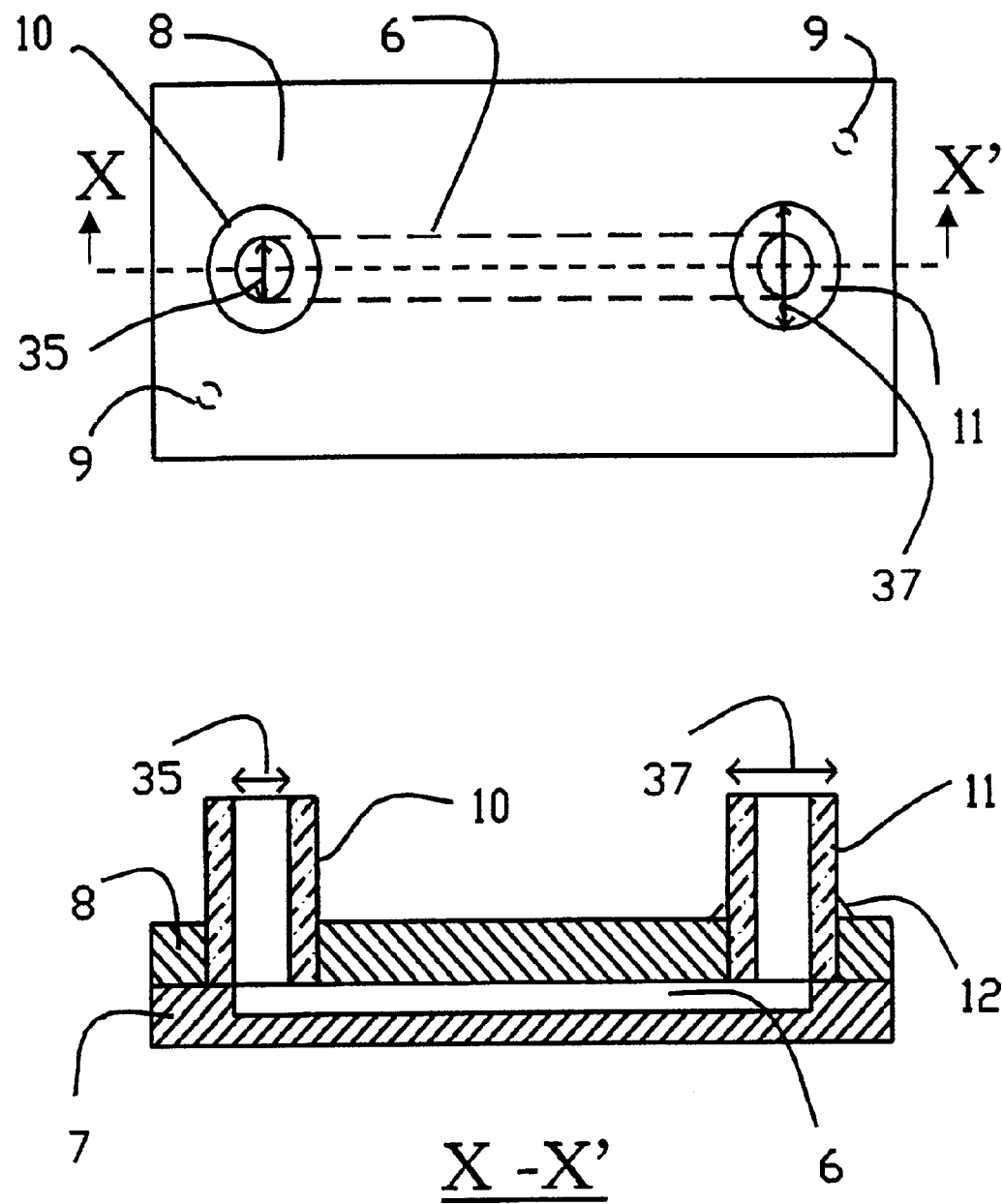
FIG. 3A shows top and section schematic views of a microfluidic lab-on-a-chip device allowing sample injection and separation to be carried out in a single buried channel.
Figure 3B:
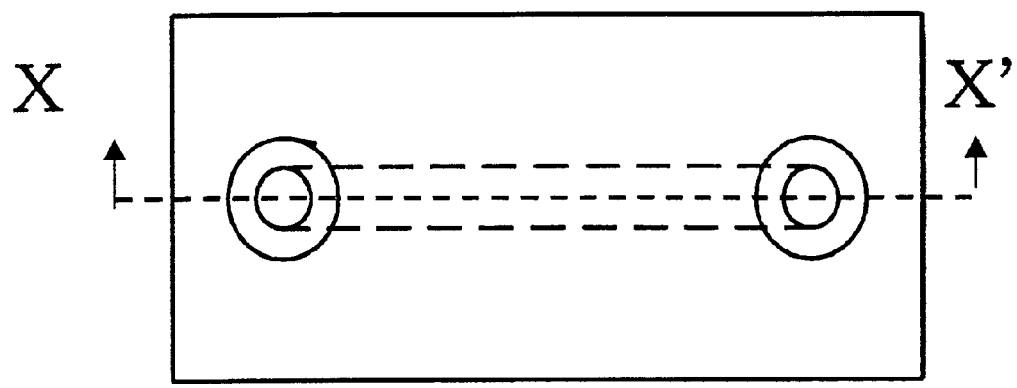
FIG. 3B shows top and section schematic views of a microfluidic lab-on-a-chip device allowing sample injection and separation to be carried out in a single raised channel.

FIG. 3A shows a microfluidic device that allows sample injection and separation to be carried out in a single buried channel. Capillaries 10 and 11 are positioned in the access ports, which are aligned with the channel 6. The capillaries are sealed to the access port openings with sealant 12. Sample injection into the single channel is through one of the capillaries 10 or 11 inserted in the access ports 5 in the cover piece. Adhesive sealant 12 may be used on junction of the capillaries and the access ports to prevent fluid leakage from the microfluidic channel to the outside.

As shown in FIG. 3A, the capillaries have an inner diameter (ID) 35 and an outside diameter (OD) 37. The OD and the diameter of the access port are approximately equal. This provides a tight fit between the access port opening and the capillary. An adhesive may be placed around the perimeter of the capillary at the junction with the access port to improve the seal of the connection and prevent fluid leakage.

The capillary may be a standard capillary commonly used in capillary electrophoresis or micro HPLC, i.e. silica tubing with an outer coating of polymer. Other types of capillaries, preferably made of polymers, may also be used. The capillary may be made of the same polymer as the substrate or a different material. The capillary may also be optically transparent. Preferably, the end of the capillary inside the access port does not protrude beyond the thickness of the substrate in which the access port resides.

Likewise FIG. 3B shows a microfluidic device that allows sample injection and separation to be carried out in a single microfluidic channel 56 with raised walls 44.

Figure 3B:
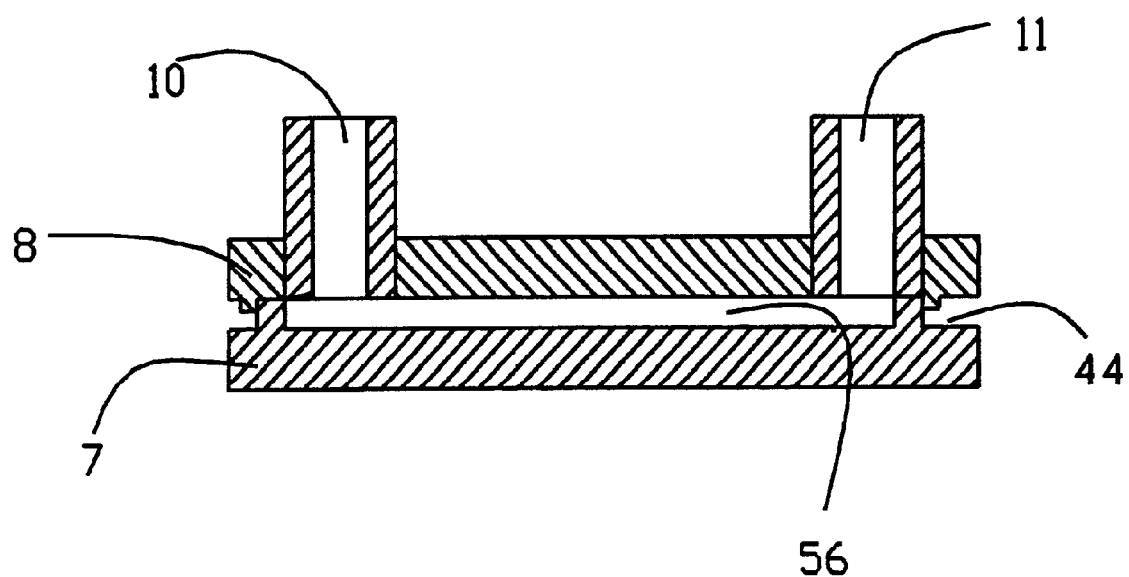

Shown in FIG. 4, is a device with an access port 13 in the channel bottom. This access port is positioned inside the microfluidic channel itself, whereas the access ports shown in FIGS. 2 and 3 are positioned in the device cover to allow access to the channel. The capillary 14 is inserted in the access port 13 to provide sample injection or a connection to other devices or elements within the same device.

At least two access ports with capillaries inserted as described above are typically needed for each channel, as shown in FIG. 4. In one example, one access port provides a capillary to inject a sample. The open end of this capillary is immersed in a sample reservoir that may or may not be an integral part of the microfluidic device. Additionally, the open end of another capillary is likewise immersed in another external reservoir. Either electrokinetic flow or pressure flow is induced to drive the fluid from the sample reservoir into the microfluidic channel. Likewise fluid can be driven from a channel on one substrate into another channel on the surface of another substrate if the channels are connected through the access ports extending through the thickness of the first substrate.

Figure 5:
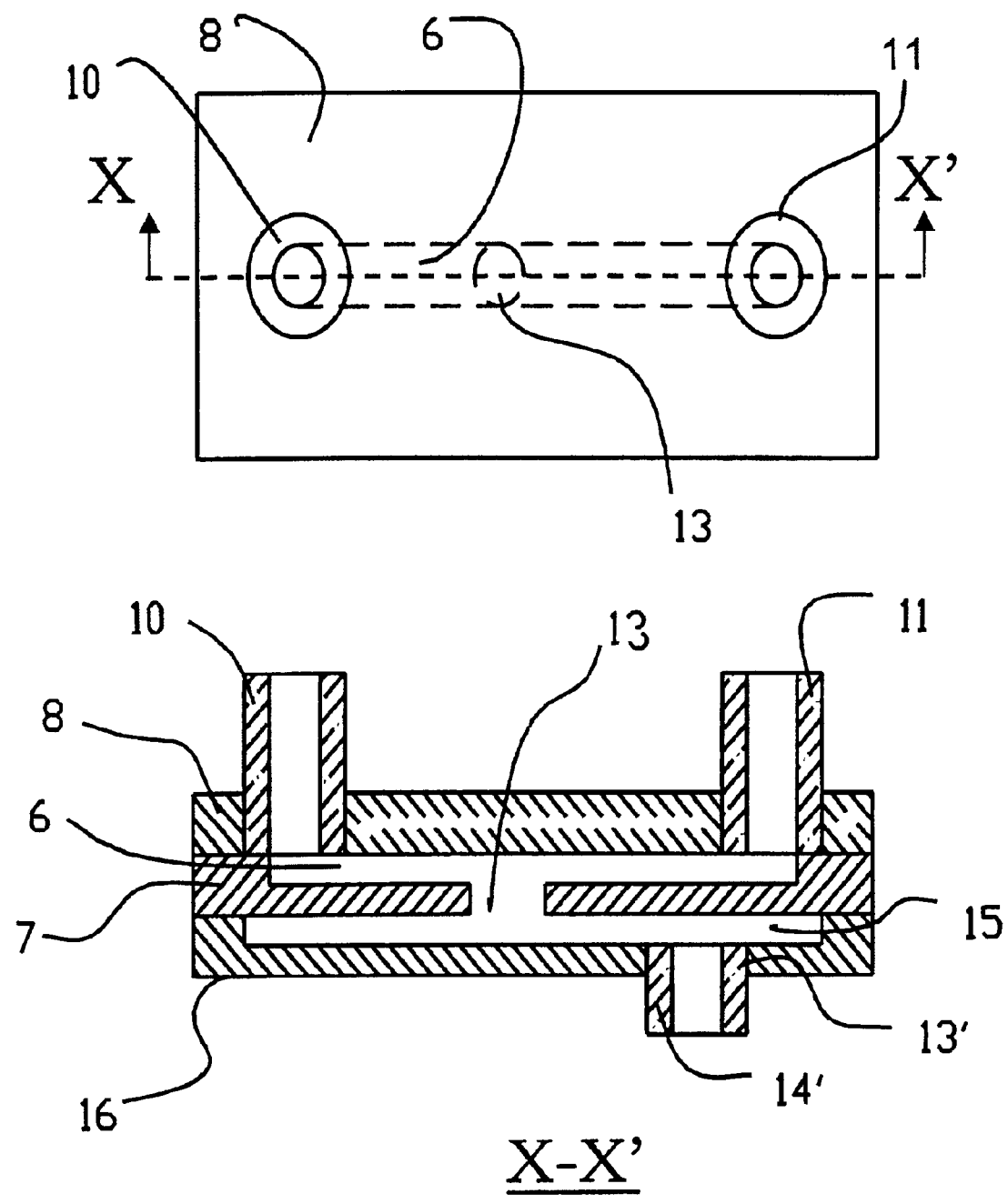
FIG. 5 shows a schematic of a microfluidic lab-on-a-chip device with a hole interconnecting two microfluidic channels.

Referring to FIG. 5, a similar microfluidic device as in FIG. 4 is illustrated. The access port 13 in the microfluidic channel 6 shown in FIG. 5 is connected to another microfluidic feature, in this case, another microfluidic channel 15 in a second substrate 16. The secondary channel 15 may or may not be connected to other devices through an access port 13' and a capillary 14'. Additional layers of substrates comprising various microfluidic features may be combined in this method. By stacking the microfluidic devices, sophisticated microfluidic architectures can be accommodated in devices that require minimal width and length, but provide adequate device operating space though multiple layers of substrates.

In another configuration, individual microfluidic channels in the same device or in separate devices may be connected with capillaries. This is analogous to 'jumpering' in electronic circuits. Using capillaries to provide connections on microfluidic devices greatly enhances the applications of these devices, as various operations can be interconnected. For example, a polymer device for separation may be connected to a silicon-based device with a heater or other built-in functions for use in the same chemical or biochemical process. The jumper-connection concept facilitates experimenting with various device configurations before committing to a final architecture for a device involving a series of processes. This provides a microfluidic device equivalent to breadboarding in conventional electronic circuits. To extend the utility of these devices, common reservoirs containing a variety of liquids such as samples and buffers may be fed to different channels through capillaries. The capillaries may easily be connected or disconnected during the optimization of the device design.

Figure 6:
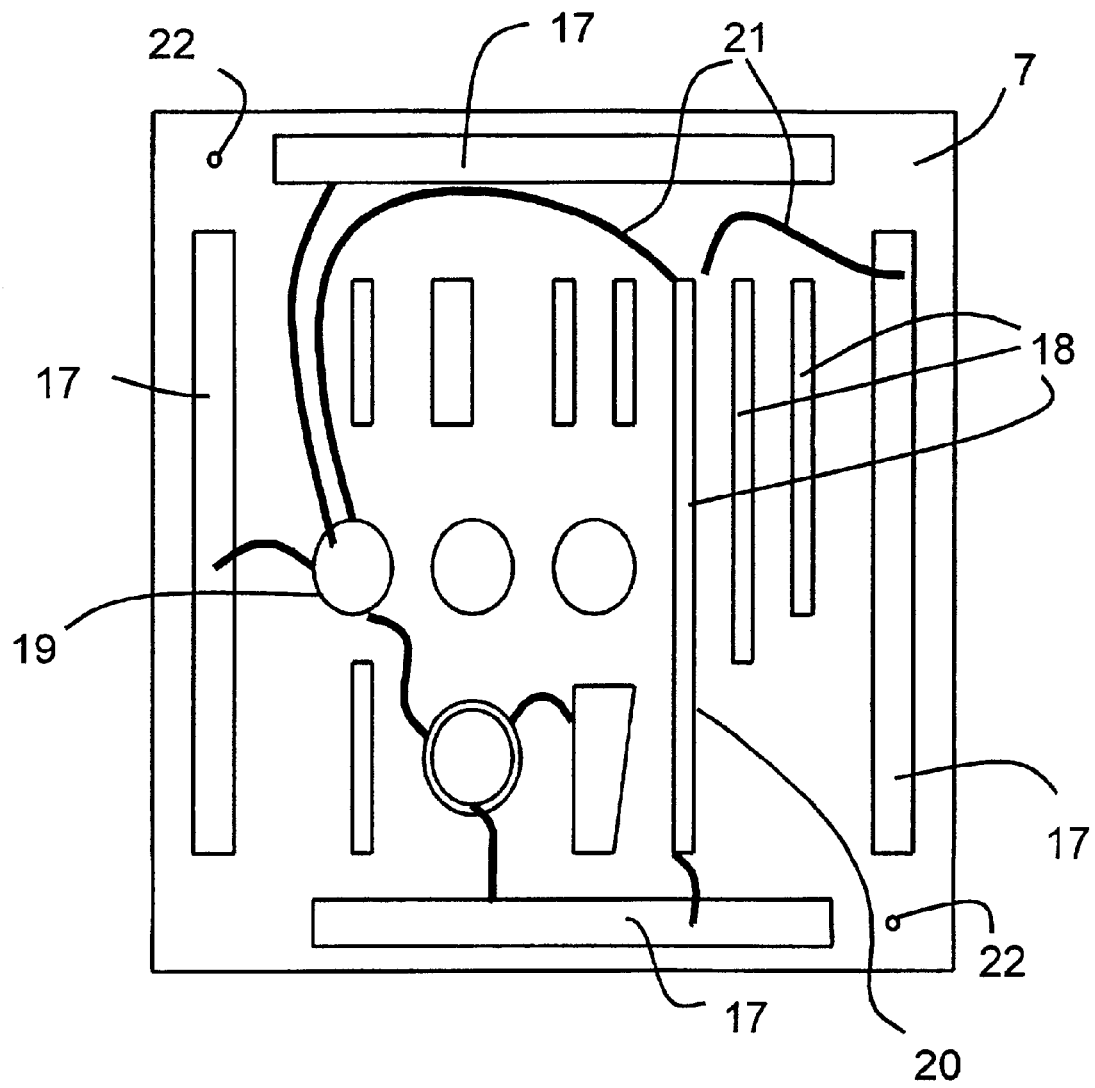
FIG. 6 shows a schematic of a complex microfluidic device having interconnecting components assembled in a "breadboard" type of configuration, with capillary interconnections of the operating components.

Referring to FIG. 6, a possible configuration of various microfluidic devices is shown with common reservoirs 17 for samples, buffers, mobile phases, waste, etc. A variety of microfluidic features such as channels 18 of different widths, depths and lengths, a microreactor 19 and a detector window 20 are indicated. Other possible microfluidic features may also be incorporated into the device through capillary connections 21. The positions of these various microfluidic features are flexible. Capillaries 21 connect one element to another in accordance with the particular application. The devices may also have covers with access ports that accommodate the capillaries. As previously described, the cover and the substrate align with alignment devices 22.

Figure 7:
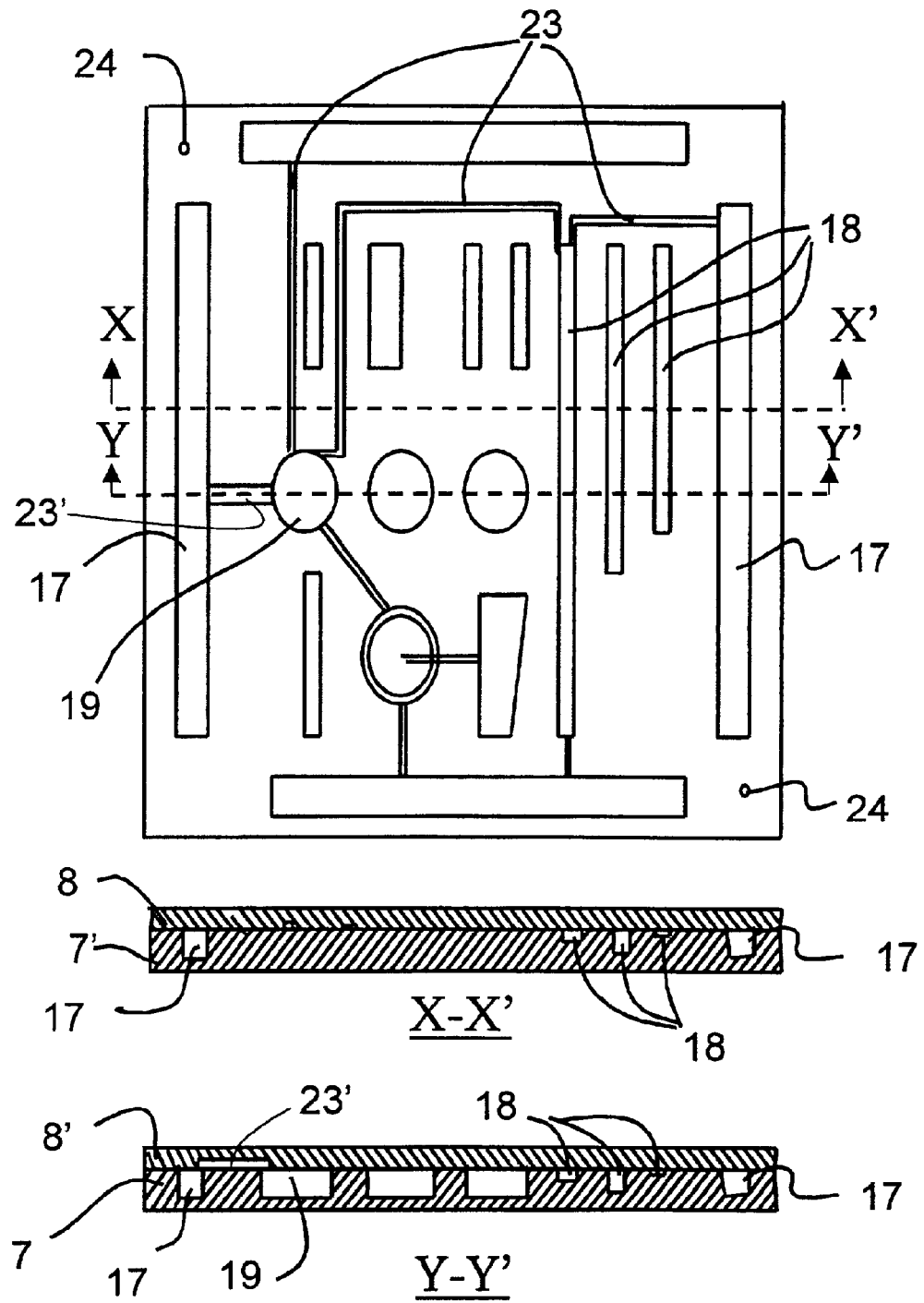
FIG. 7 shows a schematic of a complex microfluidic device having interconnecting components assembled in a "breadboard" type of configuration, with interconnections of the operating components being provided by interconnecting ducts in the cover.

The cover may also contain interconnecting ducts 23, as shown in FIG. 7. The interconnecting ducts 23 formed in the cover 8' of FIG. 7 replace the interconnecting capillaries 21 shown in FIG. 6. These interconnecting ducts are formed on the surface of the cover 8' that interfaces the substrate 7' such that fluid may flow between the cover piece 8' and the top surface of the substrate. All of the microfluidic features shown in FIG. 7 are interfacial structures between the cover and the substrate. As previously described, the cover 8' and the substrate 7' are aligned by alignment devices 24. While not shown explicitly, the cover may also contain analytical channels.

In addition to the top view of a microfluidic device, two section views of the same microfluidic device are also illustrated in FIG. 7. The view across the X-X' section reveals the substrate reservoir 17 and channel 18, as well as the interconnecting ducts 23 of the cover piece 8'. The view across the Y-Y' section also reveals the substrate reservoir 17 and channel 18, in addition to a microreactor 19 in the substrate. The interconnecting duct 23' of the cover is visible in the Y-Y' view connecting the microreactor 19 to one of the reservoirs.

Examples of components that may be incorporated into devices such as those described above in FIG. 1 through 7 include, but are not limited to, electrophoresis channels, reservoirs, access ports, nozzles for electrospray ionization for mass spectrometry, for MALDI (matrix assisted laser desorption/ionization) spotting applications, and for use with microtiter plates, windows for the detection of ultra-violet or visible signals, including for example fluorescence and chemiluminescence. Such components find potential use in protein separation applications, among others.

As can be appreciated from the foregoing discussion, the design of microfluidic devices can be a complex process requiring integrating a possibly large number of operating components. The fact that the resulting device may have interconnections constituting a 3-dimensional matrix of components that are unfamiliar to the individual seeking the design, adds to the difficulty of coming up with an appropriate configuration. This type of task can, however, be handled very well by computer-aided design systems.

Design, Ordering, and Manufacturing

Figure 8:
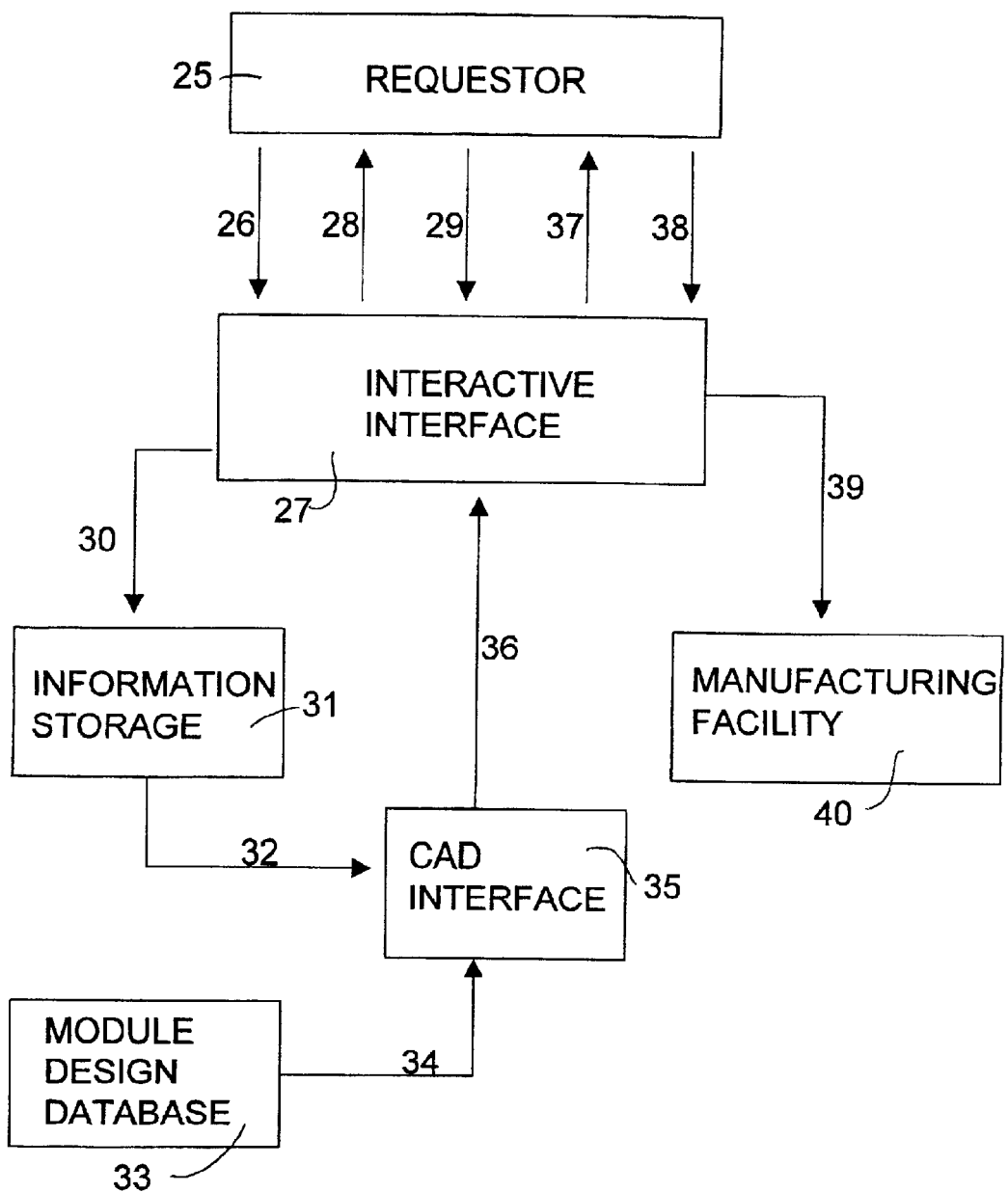
FIG. 8 shows a schematic flowchart of the invention, indicating the sequence of steps taken and the interactions of the various methods and means used.

The methods and systems of the invention can best be understood by reference to the flow chart in FIG. 8, which shows the elements of the process for designing, ordering, and manufacturing microfluidic devices.

The method is initiated when a request 26 is received from a requestor 25 for a configuration for a microfluidic device. This, and the steps up to and including the delivery of a microfluidic device, may be performed by any individual at any location. Typically requester 25 is a customer, who contacts a provider of microfluidic devices, who designs and arranges for the delivery of the device using the methods of this patent. The request for a microfluidic device configuration is made over a computer information network, for example by logging in from a remote computer to an Internet site, which makes available an interactive interface 27 for prompting the requester.

The interactive interface, resident on the provider's computer or on one accessed by the provider, sends a series of questions 28 regarding the functional specifications required for each component to be included in the device, as well as a scale specification for each component, indicating the size or capacity of the component. Sufficient questions are asked to clarify the temporal sequence of the functions performed by the various components. The requestor may then provide answers 29 to these questions, for example over an Internet or other network connection. The information provided by these answers is then stored 30 in an information storage device 31, typically computer memory.

A component design database 33 is provided, comprising information on a variety of available microfluidic components. Information from this database is then accessed 34 by a computer-assisted design (CAD) interface 35, which also receives information 32 from the information storage device 31, to generate a configuration for the microfluidic device. The CAD interface may be on a computer operated by the provider, or resident on another computer in communication with the provider's computer. Information defining the configuration for the microfluidic device is then communicated 36 via interactive interface 27 to the requestor 25, in the form of a visual display on his computer.

If the design shown in the visual display does not meet the requestor's desires, interactive interface 27 may optionally receive additional information 29 from the requester and process it as described above for a second iteration of the design, or for any number of iterations, until a satisfactory design is achieved. Once the visual display meets the requested design, interactive interface 27 may receive a purchase order 38, such as an electronic purchase order, for one or more devices thus configured, and may then send the configuration information 39 to manufacturing facility 40, which in a preferred embodiment is equipped with a computer-aided manufacturing (CAM) interface in communication with CAD interface 35. Manufacturing facility 40 then makes the one or more devices ordered.

Various CAD programs are known in the art for designing and modeling any number of products. For example, software made by SolidWorks Corporation, of Concord, Mass., focuses specifically on mechanical design to help manufacturers get products to market faster. One offering, known as 3D PARTSTREAM.NET, makes available to a parts manufacturer the ability to provide what is essentially a digital catalog of parts with predefined specifications, using a CAD format which allows a requester to more easily adapt his designs to use already-available parts. Such a CAD system may be used to carry out an exemplary embodiment of the invention.

The computer-assisted manufacturing (CAM) system allows direct and exact conversion of the configuration to a fabricated microfluidic device. CAM systems are well known in the art, as a large variety of them is used in conjunction with all computer numerical control (CNC) machine tools. For example, one is available from BobCad CAM, San Jose, Calif. Microfluidic devices according to the configurations created by the methods of this invention can be manufactured by methods and techniques such as those described in U.S. patent application Ser. No. 10/061,001 to Staats, filed Jan. 30, 2002, incorporated herein by reference. Such methods include injection molding of a suitable thermoplastic, compression molding and casting of a wide range of polymers, and direct forming using ink-jet technology.

Because finding the optimal configuration for a microfluidic device may require actual testing and-then modifying the device, the requestor may experimentally use a first design provided by the method described above, and then make refinements to the design in a subsequent visit to the provider's site on the computer network. Thus for example additional information 29 shown in FIG. 8 may be provided by the requestor after a first iteration has been manufactured and tested. The site may keep the customer's information on file so that subsequent modifications can be made from a set of existing parameters.

The advantageous properties of the invention can be observed by reference to the foregoing descriptions of various embodiments, which illustrate but do not limit the invention.

INDUSTRIAL APPLICABILITY

The invention is especially useful for the facile design and manufacture of customized microfluidic devices, based on input from an individual who is able to specify the requirements of what the device will do, but who is unwilling and/or unable to design and/or build a device for himself. Thus it affords the benefit of extending microfluidic experimental capability to a large number of individuals who would otherwise find it difficult to perform microfluidic experiments.

Having described the invention, we now claim the following and their equivalents.

What is claimed is:

1. A method for designing a microfluidic device, the method comprising the steps of: (a) providing an interactive interface, accessible over a computer information network, for designing one or more microfluidic devices, (b) receiving from a requester at the interactive interface via the computer information network a request to design a microfluidic device; (c) prompting the requestor for information about desired operational steps to be performed by the microfluidic device; (d) receiving and storing the information about the desired operational steps from the requestor; (e) providing a CAD interface having access to a database of microfluidic device component designs corresponding to a plurality of operational steps performable by microfluidic devices; (f) using the CAD interface to generate a visual display of the microfluidic device viewable by the requestor via the computer information network, the visual display compiled using microfluidic device component designs corresponding to the desired operational steps for the microfluidic device; (g) performing steps (a)–(f) with respect to a first iteration of a microfluidic device, and (h) performing steps (b)–(f) with respect to a second iteration of the microfluidic device, wherein the information from step (d) with respect to the first iteration is made available to the requestor for modification in designing the second iteration.

2. The method of claim 1 wherein the information about the operational steps comprises functional information, scale information, sequence information, or a combination thereof.

3. The method of claim 1 wherein the computer information network comprises a global computer information network.

4. The method of claim 1 further comprising:
   (i) receiving at the interactive interface via the computer information network, a purchase order for the microfluidic device.

5. The method of claim 4, further comprising:
   (j) sending information defining said microfluidic device to a manufacturing facility; and (k) manufacturing said microfluidic device.

6. The method of claim 5 further comprising a step for sending said information from the CAD interface to a CAM interface.

7. The method of claim 5 wherein the manufacturing facility comprises a CAM interface in communication with the CAD interface.

8. A system for designing a microfluidic device, the system comprising: means accessible by a computer information network for providing an interactive interface for designing one or more microfluidic devices; means for receiving from a requestor a request to design a microfluidic device; means for prompting the requestor for information about desired operational steps to be performed by the microfluidic device; means for receiving the information about the desired operational steps from the requester; means for storing the information received from the requester about the desired operational steps means for storing a database of microfluidic device component designs corresponding to a plurality of operational steps performable by microfluidic devices; means for compiling a plurality of microfluidic device component designs corresponding to the desired operational steps for the microfluidic device into a visual display of the microfluidic device viewable by the requestor via the computer information network; means for storing and retrieving said information about desired operational steps, means for storing and retrieving said visual display of said device, and means for generating a second iteration of said device.

9. The system of claim 8, wherein the information about the operational steps comprises functional information, scale information, sequence information, or a combination thereof.

10. The system of claim 8 wherein the computer information network comprises a global computer information network.

11. The system of claim 8 further comprising: means for receiving a purchase order for the microfluidic device.

12. The system of claim 11 further comprising: means for sending information relating to the microfluidic device to a manufacturing facility; and means for manufacturing the microfluidic device.

13. The system of claim 12 wherein said means for manufacturing comprises a CAM interface and said means for compiling comprises a CAD interface in communication therewith.

14. A system for designing a microfluidic device, the system comprising: an interactive computer interface accessible by a computer information network for designing one or more microfluidic devices, the interactive computer interface adapted to receive from a requestor a request to design a microfluidic device, prompt the requester for information about desired operational steps to be performed by the microfluidic device, and receive information about the desired operational steps from the requestor; a first computer memory for storing the information received from the requestor about the desired operational steps a computerized database of microfluidic device component designs corresponding to a plurality of operational steps performable by microfluidic devices; and a CAD interface in communication with the interactive computer interface, the first computer memory, and the computerized database for compiling a plurality of microfluidic device component designs corresponding to the desired operational steps for the microfluidic device into a visual display of the microfluidic device viewable by the requestor via the computer information network, wherein said interactive computer interface is adapted to store and retrieve said information about desired operational steps, to store and retrieve said visual display of said device, and to generate a second iteration of said device.

15. The system of claim 14 wherein the information about the operational steps comprises functional information, scale information, sequence information, or a combination thereof.

16. The system of claim 14, wherein the computer information network comprises a global computer information network.

17. The system of claim 14, wherein the interactive computer interface is further adapted to receive a purchase order for the microfluidic device.

18. The system of claim 17 wherein the interactive computer interface is further adapted to send information defining said microfluidic device to a manufacturing facility; and wherein said facility manufactures said device.

19. The system of claim 18 further comprising a CAM interface in communication with the CAD interface for manufacturing the microfluidic device.

20. A method for providing a microfluidic device, the method comprising the steps of: (a) providing an interactive interface, accessible over a computer information network, for designing one or more microfluidic devices, (b) receiving from a requester at the interactive interface via the computer information network a request to design a microfluidic device; (c) prompting the requestor for information about desired operational steps to be performed by the microfluidic device; (d) receiving and storing the information about the desired operational steps from the requester; (e) providing a CAD interface having access to a database of microfluidic device component designs corresponding to a plurality of operational steps performable by microfluidic devices; (f) using the CAD interface to generate a visual display of the microfluidic device viewable by the requestor via the computer information network, the visual display compiled using microfluidic device component designs corresponding to the desired operational steps for the microfluidic device; (g) receiving at the interactive interface via the computer information network, a purchase order for the microfluidic device; (h) sending information defining said microfluidic device to a manufacturing facility; and (i) manufacturing said microfluidic device, comprising performing steps (a)–(f) with respect to a first iteration of a microfluidic device, and further comprising performing steps (b)–(f) with respect to a second iteration of the microfluidic device, wherein the information from step (d) with respect to the first iteration is made available to the requestor for modification in designing the second iteration, wherein the information about the operational steps comprises functional information, scale information, sequence information, or a combination thereof, the computer information network comprises a global computer information network, and the manufacturing facility comprises a CAM interface in communication with the CAD interface.

* * * * *